United States Patent [19]

Dosako et al.

[11] Patent Number: 5,147,853
[45] Date of Patent: Sep. 15, 1992

[54] INFECTION PROTECTANT

[75] Inventors: Shunichi Dosako, Urawa; Hiroko Kusano, Tokorozawa; Eiki Deya, Sayama; Tadashi Idota, Kawagoe, all of Japan

[73] Assignee: Snow Brand Milk Products Co., Ltd., Sapporo, Japan

[21] Appl. No.: 604,333

[22] Filed: Oct. 26, 1990

Related U.S. Application Data

[63] Continuation of Ser. No. 191,252, May 6, 1988, abandoned.

[30] Foreign Application Priority Data

May 15, 1987 [JP] Japan .................. 62-118612

[51] Int. Cl.$^5$ .................. A61K 37/16; A61K 33/42; C07K 15/14
[52] U.S. Cl. .................. 514/7; 514/8; 514/2; 514/21; 530/322; 530/360; 530/395; 530/391.1; 530/409; 530/411; 435/41; 435/68.1
[58] Field of Search .................. 514/2, 8, 21, 7; 530/322, 360, 395, 409, 411; 435/391.1, 41, 68.1

[56] References Cited

U.S. PATENT DOCUMENTS

| | | |
|---|---|---|
| 4,007,264 | 2/1977 | Queuille et al. |
| 4,042,575 | 8/1977 | Eustache . |
| 4,213,896 | 7/1980 | Davis .................. 530/360 |
| 4,427,658 | 1/1984 | Maubois et al. .................. 514/2 |
| 4,462,990 | 7/1984 | Jolles et al. .................. 514/21 |
| 4,495,176 | 1/1985 | Brule et al. .................. 514/7 |
| 4,762,822 | 8/1988 | Ettinger .................. 514/25 |
| 5,063,203 | 11/1991 | Drouet et al. .................. 514/8 |

OTHER PUBLICATIONS

The Merck Index 9th edition 1976, No. 1879.
The Merk Index, 9th ed, p. 562.

*Primary Examiner*—Christine M. Nucker
*Assistant Examiner*—Kay K. Kim
*Attorney, Agent, or Firm*—Oblon, Spivak, McClelland, Maier & Neustadt

[57] ABSTRACT

Disclosed herein is an infection protectant which is excellent in infection protective effects and is also safe. κ-Casein, a sialic-acid-conjugated protein derived from cow milk, and a glycomacropeptide derived from κ-casein, each of which is useful as an active ingredient in this invention, have been found to be effective for the prevention of adhesion of *E. coli* on cells and also for the inhibition of transformation of lymphocytes by EBV and also to have strong HI activity against virus. The infection protectant of this invention is hence believed to exhibit marked effects for the prevention of occurrence of infectious diarrhea, for mass protection against spreading of influenza, and also against canceration of lymphocytes. Since the active ingredient of the infection protectant is a substance derived from cow milk, it is free of any problem from the viewpoint of safety. Moreover, it is absolutely tasteless and odorless. It can therefore be added to foods for its application.

1 Claim, No Drawings

INFECTION PROTECTANT

This application is a continuation of application Ser. No. 07/191,252, filed on May 6, 1988, now abandoned.

BACKGROUND OF THE INVENTION

1. Field of the Invention

This invention relates to an infection protectant useful for the prevention of infectious diseases caused by pathogenic bacteria or virus.

2. Description of the Prior Art

Antibiotics have heretofore been used for the treatment of infectious diseases caused by pathogenic bacteria. Although their effects are remarkable, their administration to allergic subjects may lead to death from shock and similar problems. In many instances, substantial limitations are therefore imposed upon their application.

It is generally practised to administer a vaccine against an infectious disease caused by virus. Since virus itself tends to undergo mutation or the like, it is not seldom that vaccination does not work well. Regarding influenza virus in particular, the type of virus which spreads changes every year and mass vaccination for schoolchildren and the like is considered to be almost meaningless.

There is hence a strong demand for the development of an infection protectant which gives no adverse effects to allergic subjects and does not lose its preventive effects by mutation of virus.

Incidentally, it has been reported that certain non-specific hemagglutination inhibition factors are contained in human milk and cow milk also have similar activities as the above factors although not so strong as human milk [Saito, et al., "Agricultural Biological Chemistry", 36. 1437–1439 (1972)]. It has hence been assumed that cow milk also contains one or more substances which undergo a direct interaction with the receptors of pathogenic bacteria or virus.

Oligosaccharides and ganglioside, which contain N-acetylneuraminic acid, have conventionally been known as such substances. They are believed to prevent infection by undergoing an interaction with the receptors of pathogenic bacterial or virus.

However, these substances have a small molecular weight. It is therefore essential to administer them in a substantial amount in order to allow them to undergo an interaction with all receptors for the exhibition of their effects. They are hence not practical.

Namely, no infection protectant having sufficient effects and safety has yet been realized.

BRIEF SUMMARY OF THE INVENTION

With the foregoing in view, the present invention has as a principal object the provision of an infection protectant which has protective effects against infectious diseases caused by pathogenic bacteria or virus, does not lose its effects by mutation of the like of the bacteria or virus and involves absolutely no problem in safety.

It is a principal feature of the infection protectant of the present invention that a sialic-acid-conjugated protein derived from cow milk is contained either as is or in a form treated beforehand with a protease.

DETAILED DESCRIPTION AND THE PREFERRED EMBODIMENTS

The sialic-acid-conjugated protein useful as an active ingredient in the present invention is a glycoprotein in a form conjugated with sialic acid which is contained in cow milk, and κ-casein, lactoferrin and the like have been known by way of example [Kobata, "The Glycoconjugates I", page 423, Academic Press Inc. (1977)]. In particular, κ-casein has a sialic acid content as much as 2 g/100 g or more and has high infection protective effects.

Further, the sialic-acid-conjugated peptide also useful as an active ingredient is a fraction obtained by treating the above sialic-acid-conjugated protein with a peptidase. Especially, a glycomacropeptide (hereinafter abbreviated as "GMP") obtained by causing rennet to act on κ-casein has a sialic acid content as high as 5 g/100 g or more and has particularly high infection protective effects.

The sialic-acid-conjugated protein may be obtained from cow milk by a known process [H. A. McKenzie, "Milkproteins", Academic Press Inc. 1971]. As a process for the industrial production of κ-casein, it has been known, for example, to fractionate sodium caseinate by subjecting crude liquid to gel filtration under low ionic strength (Japanese Patent Laid-Open No. 91848/1984).

On the other hand, the sialic-acid-conjugated peptide can be obtained by causing a protease to act on the sialic-acid-conjugated protein obtained from cow milk by a method known per se in the art and then subjecting the resultant product to one or more factionation methods such as gel filtration, ion-exchange chromatography and/or affinity chromatography so as to fractionate the sialic-acid-conjugated peptide.

Any protease may be used as the above protease, so long as it belongs to the group of endopeptidases. Pepsin, trypsin, papain, chymotrypsin, pronase, rennet, pancreatine, ficin and the like may be mentioned by way of example.

Among such sialic-acid-conjugated peptides, GMP can be obtained with a high purity by adjusting the pH of κ-casein, cow milk, reconstituted milk or casein to pH 5.5–5.6, adding rennet in a proportion of 1/5,000–1/50 (w/w) based on the protein, reacting them at 30°–45° C. for 30–3 hours, heating the resultant reaction mixture to inactivate the rennet, cooling it to 40° C., adding 5 mM or more of calcium to cause components other than GMP to precipitate, collecting the supernatant and concentrating same, optionally desalting the solution, and then drying the solution.

In this invention, a sialic-acid-conjugated protein obtained in the above-described manner, for example, κ-casein or GMP is used as an active ingredient for the infection protectant.

In order to use such an active ingredient as an infection protectant, it may be administered, for example, at a dose of 2.5 mg/kg/day or more in the case of κ-casein and at a dose of 0.5 mg/kg/day or more in the case of GMP. Infection by pathogenic bacteria or virus can be prevented by this administration.

Infection protective effects of the present invention will next be described on the basis of specific test results.

(1) Preventive effects against adhesion of *E. coli* to human epithelial cells

Procedure

E. coli strains, Type 055 (ATCC 12014) and Type 0111a,111b (ATCC 29552) cultured separately in heart infusion medium were suspended separately in Eagle's culture medium to give a concentration of $10^8$ cells per ml.

κ-Casein and GMP were separately added at concentrations of 0.01%, 0.1% and 1% to the above-prepared E. coli suspensions. The resultant suspensions were added separately to 407 Strain which had been derived from the human small intestine and was maintained in an ascitics form in Eagle's culture medium. They were reacted at 30° C. for 1 hour.

After the reaction, the number of E. coli cells adhered on 50 cells of 407 Strain in each sample was counted microscopically.

Adhesion percentage (A) for each sample was calculated in accordance with the following equation:
$$A = X_s/X_o \times 100(\%)$$

in which $X_o$ means the number of E. coli cells adhered in control and $X_s$ denotes the number of E. coli cells adhered in the sample.

Results are shown in Table 1.

TABLE 1

| Active ingredient in sample | Concentration (%) | Adhesion percentage (A) of E. coli (%) | |
|---|---|---|---|
| | | ATCC 12014 | ATCC 29552 |
| κ-Casein | 0.01 | 70.3 | 68.8 |
| | 0.1 | 7.5 | 7.4 |
| | 1 | 3.7 | 2.2 |
| GMP | 0.01 | 11.4 | 9.5 |
| | 0.1 | 4.5 | 1.8 |
| | 1 | 4.3 | 1.8 |

As envisaged from Table 1, preventive effects for the adhesion of E. coli on human epithelial cells were observed at the concentration of 0.1% in the case of κ-casein and at the concentration of 0.01% in the case of GMP.

(2) Hemagglutination inhibitory (HI) effects

Procedure

Using influenza A (Niigata strain) and influenza B (Singapore strain), the HI activities of κ-casein and GMP dissolved at a concentration of 1% respectively were investigated by a usual method. The results are shown in Table 2.

TABLE 2

| Active ingredient in sample | HI potency |
|---|---|
| κ-Casein | 1:2.048 |
| GMP | 1:1.024 |

As is envisaged from Table 2, both samples showed strong HI activity.

(3) Preventive effects against transformation of lymphocytes by Epstein-Barr virus (EBV)

Peripheral blood lymphocytes (PBL) collected from a normal donor were suspended at $4 \times 10^5$ lymphocytes/ml in RPMI 1640 medium which contained 10% of fetal calf serum (FCS). EBV diluted with the same medium was then added to the resultant suspension in such an amount that the concentration of EBV became 10% (v/v). In addition, 10 μl of each sample solution was added. The resultant liquid mixtures were separately poured in 20 μl portions into five wells per sample of a 96-well microtiter plate. EBV was cultured at 37° C. under an atmosphere of 5% carbon dioxide. Two weeks later, the medium was replaced. In the third week, it was determined whether transformation had taken place or not in each well. The results are summarized in Table 3.

TABLE 3

| Sample | | Transformation of lymphocytes by EBV | | | |
|---|---|---|---|---|---|
| | | EBV concentration (dilution) | | | |
| | | $10^{-1}$ | $10^{-2}$ | $10^{-3}$ | $10^{-4}$ |
| Control | | 5/5 | 5/5 | 5/5 | 5/5 |
| κ-Casein | 1 μg/ml | 5/5 | 5/5 | 3/5 | 2/5 |
| | 10 μg/ml | 5/5 | 5/5 | 2/5 | 0/5 |
| GMP | 1 μg/ml | 5/5 | 1/5 | 0/5 | 0/5 |
| | 10 μg/ml | 5/5 | 1/5 | 0/5 | 0/5 |

As is understood from Table 3, the preventive effects for the EBV-induced transformation were observed at the concentration of 10 μg/ml in the case of κ-casein and at the concentration of 1 μg/ml in the case of GMP.

EXAMPLE

κ-Casein isolated from cow milk and GMP fractionated from κ-casein were used as active ingredients. As test animals, 35 Wister rats having a body weight of about 200 g were divided by 5 rats into 7 groups. One group was used as control. The remaining 6 groups were halved further so that three groups were used as κ-casein administered groups and the remaining three groups were used as GMP administered groups. The rats of the former three groups were forced to take κ-casein at doses of 0.1, 0.5 and 1 mg/day respectively, while the rats of the latter three groups were forced to take GMP at the same doses respectively, both, using oral feeding tubes.

The rats in each group were then administered orally with a predetermined amount of ATCC 12014, pathogenic E. coli to investigate the morbidity rate of diarrhea. The results are summarized in Table 4.

TABLE 4

| Sample | Dose (mg/day) | Morbidity rate of diarrhea (%) |
|---|---|---|
| Control | — | 100 |
| κ-Casein | 0.1 | 60 |
| | 0.5 | 20 |
| | 1.0 | 0 |
| GMP | 0.1 | 20 |
| | 0.5 | 20 |
| | 1.0 | 0 |

As envisaged from Table 4, the morbidity rate was clearly low in the κ-casein administered groups and GMP administered groups. Sufficient effects were observed at the dose of 0.5 mg/day in the case of κ-casein and at the does of 0.1 mg/day in the case of GMP.

We claim:

1. A method for protection against gastrointestinal bacteria. Epstein-Barr virus and influenza viruses that comprises administering an effective amount of an isolated and purified sialic acid-conjugated protein derived from cow milk to a patient in need thereof wherein said sialic acid-conjugated protein is a κ-casein.

* * * * *